United States Patent
Binette et al.

(10) Patent No.: US 9,643,059 B2
(45) Date of Patent: May 9, 2017

(54) GOLF BALL INCORPORATING ULTRA VIOLET LIGHT RESISTANT AND LIGHT STABLE LAYER(S) AND METHOD OF MAKING

(71) Applicant: Acushnet Company, Fairhaven, MA (US)

(72) Inventors: Mark L. Binette, Mattapoisett, MA (US); Shawn Ricci, New Bedford, MA (US)

(73) Assignee: Acushnet Company, Fairhaven, MA (US)

( * ) Notice: Subject to any disclaimer, the term of this patent is extended or adjusted under 35 U.S.C. 154(b) by 0 days.

(21) Appl. No.: 14/723,528

(22) Filed: May 28, 2015

(65) Prior Publication Data

US 2016/0346620 A1 Dec. 1, 2016

(51) Int. Cl.
| | |
|---|---|
| *A63B 37/00* | (2006.01) |
| *C08J 7/02* | (2006.01) |
| *B32B 27/24* | (2006.01) |
| *A63B 45/00* | (2006.01) |
| *B05B 5/00* | (2006.01) |
| *C08K 5/3475* | (2006.01) |

(52) U.S. Cl.
CPC ...... *A63B 37/0024* (2013.01); *A63B 37/0022* (2013.01); *A63B 37/0023* (2013.01); *A63B 45/00* (2013.01); *B05B 5/00* (2013.01); *B32B 27/24* (2013.01); *C08J 7/02* (2013.01); *C08K 5/3475* (2013.01); *C08K 2201/013* (2013.01)

(58) Field of Classification Search
None
See application file for complete search history.

(56) References Cited

U.S. PATENT DOCUMENTS

| | | | |
|---|---|---|---|
| 3,961,965 A | 6/1976 | Zwahlen | |
| 4,204,879 A | 5/1980 | Paskins et al. | |
| 4,442,282 A | 4/1984 | Kolycheck | |
| 4,679,794 A | 7/1987 | Yamada et al. | |
| 4,679,795 A | 7/1987 | Melvin et al. | |
| 4,798,386 A | 1/1989 | Berard | |
| 4,802,674 A | 2/1989 | Kitaoh | |
| 4,861,664 A * | 8/1989 | Goossens | C08J 7/065 427/160 |
| 4,865,326 A | 9/1989 | Isaac et al. | |
| 5,156,405 A | 10/1992 | Kitaoh et al. | |
| 5,459,220 A | 10/1995 | Kennedy | |
| 5,487,914 A * | 1/1996 | Gerlock | B05D 3/107 427/140 |
| 5,494,291 A | 2/1996 | Kennedy | |
| 5,580,323 A | 12/1996 | Sullivan | |
| 6,506,851 B2 | 1/2003 | Wu | |
| 6,518,358 B1 | 2/2003 | Wu | |
| 6,528,578 B2 | 3/2003 | Wu | |
| 6,939,939 B2 | 9/2005 | Slegel et al. | |
| 7,148,278 B2 | 12/2006 | Bulpett et al. | |
| 2009/0062037 A1* | 3/2009 | Ohama | A63B 37/0003 473/378 |
| 2009/0075758 A1* | 3/2009 | Nakamura | A63B 37/0023 473/378 |
| 2012/0100935 A1 | 4/2012 | Michalewich et al. | |
| 2013/0323512 A1* | 12/2013 | Ichikawa | B05D 7/02 428/423.3 |
| 2014/0073458 A1 | 3/2014 | Michalewich et al. | |

OTHER PUBLICATIONS

Chemical Book; TINUVIN 571#23328-53-2.
Songsord 3280; Songwon; Aug. 18, 2006.

* cited by examiner

*Primary Examiner* — David Buttner
(74) *Attorney, Agent, or Firm* — Margaret C. Barker

(57) ABSTRACT

A golf ball comprising a layer formed from at least one of a thermoset material or a thermoplastic material throughout; the layer having a treated region and an untreated region; the treated region extending inward from an outer surface of the layer and comprising a UV resistance composition; and the untreated region not comprising the UV resistance composition. For example, the treated region may be infused with the UV resistance composition. The layer may be a cover or even an inner golf ball layer, which can sometimes become exposed during play. The UV resistance composition may be formed from a mixture of an ultraviolet light absorber (UVA) and a solvent, the UVA being selected from benzotriazole type stabilizers, hindered amine type stabilizers, phenolic type stabilizers, triazines, or combinations thereof, and the solvent comprising at least one of acetone, methyl ethyl ketone, methyl isobutyl ketone, ethyl acetate, or butyl acetate.

16 Claims, No Drawings

GOLF BALL INCORPORATING ULTRA VIOLET LIGHT RESISTANT AND LIGHT STABLE LAYER(S) AND METHOD OF MAKING

FIELD OF THE INVENTION

The present invention is directed to golf balls that are ultraviolet (UV) light resistant and formed from light stable materials and methods of making such golf balls.

BACKGROUND OF THE INVENTION

Golf balls are made in a variety of constructions and compositions. Generally, a core is surrounded by a cover, with at least one intermediate layer optionally disposed therebetween. Examples of conventional golf ball materials range from balata to polybutadiene, ionomer resins, polyurethanes, and/or polyureas. Typically, outer layers are formed about the spherical outer surface of an inner golf ball component via compression molding, casting, or injection molding.

Golf ball manufacturers continuously experiment with constructions and material formulations in order to target and improve aerodynamic and/or inertial properties and achieve desired feel without sacrificing durability or aesthetics. In this regard, simpler and more cost effective ways are sought for preserving golf ball color appearance, which can deteriorate, for example, when a white golf ball is exposed to UV light on the course and UV degradation ensues. Such UV degradation becomes visibly apparent as golf ball yellowing/browning, which is not appealing to players who equate discoloration with lower-quality and inferior golf balls.

Golf ball finishing coats, primer coatings, and cover layers have been known to need protection from exposure to UV light. Finishing coatings are often clear coats, so that any underlying primer coating or cover layer could also be directly exposed to UV light on the course. Regardless, inner surfaces are also sometimes partially exposed to UV light when nicks or abrasions occur in the golf ball surface when a club face (e.g. an iron) strikes the golf ball.

Certain golf ball materials such as polyurethane-based compositions are particularly vulnerable to UV degradation. Manufacturers have encountered the tendency of elastomers to react with molecular oxygen in a degradation process called "autoxidation." This degradation process results in undesirable changes, such as product discoloration and loss of physical properties. Autoxidation may be initiated by heat (thermo-oxidative degradation), high energy radiation (photodegradation), mechanical stress, catalyst residues, or through reaction with other impurities. However, photodegradation by ultraviolet ("UV") radiation is believed to be the most damaging of these autoxidation mechanisms. Thermo-oxidation and photodegradation processes are initiated with the formation of free radicals. These free radicals react rapidly with oxygen to from peroxy radicals. These peroxy radicals may further react with the polymer chains leading to the formation of hydroperoxides. On exposure to additional heat or light, hydroperoxides decompose to yield more radicals that can reinitiate the degradation process.

UV absorbers protect against photodegradation by "competing" with the polymer for absorption of ultraviolet light. An ideal UV absorber should be very light stable and should have broad, intense absorption over the UV range from about 290 nm to 400 nm. Antioxidants, on the other hand, interrupt the degradation process in different ways according to their structure. The major classifications of antioxidants are primary antioxidants and secondary antioxidants. Primary antioxidants, such as sterically hindered phenols, react rapidly with peroxy radicals (ROO) to break the degradation cycle. Secondary antioxidants, such as arylamines, are more reactive toward oxygen-centered radicals than are hindered phenols. The secondary antioxidants react with hydroperoxide (ROOH) to yield non-radical, non-reactive products, and are frequently called hydroperoxide decomposers.

The color instability caused by both thermo-oxidative degradation and photodegradation typically results in a "yellowing" or "browning" of the polyurethane material, an undesirable characteristic for urethane compositions are to be used in the covers of golf balls, which are generally white.

Initially, this problem was addressed by applying at least one layer of "paint" comprising a clear and/or pigmented topcoat material about the cover material. But repeated blows to the golf ball surface with a golf club causes scuffing or paint removal tending to result in exposing the cover material to harmful UV rays during play, ultimately resulting in undesirable "yellowing" and/or "browning" of the cover material. And apart from degradation of the cover material due to direct UV radiation exposure, degradation still occurred over a long time period and the resultant discoloration tended to "bleed" through the paint layer, also discoloring the golf ball cover. This long-felt problem in the golf ball art led golf ball manufacturers to formulate UV absorbers and stabilizers directly into the cover resin material for improved color stability upon prolonged exposure to UV light—either in addition to or in lieu of the paint layer.

However, incorporating UV absorbers and stabilizers directly into the entire cover resin material in concentrations as high as 10 wt % can represent a significant unnecessary manufacturing cost given that the UV absorbers/stabilizers are really only needed in those surface areas or regions of the layer that are exposed to UV light. And additional costs can be incurred from difficulties associated with incorporating the additives into the entire batch. Meanwhile, there is a potential for adverse effect on physical properties such as loss of shear resistance or poor tensile from UV absorbers and stabilizers being added directly into the entire batch.

Thus, there is a need for golf balls and methods of making golf balls wherein UV resistant and color stable compositions may be provided onto only those golf ball surfaces that are subject to UV light exposure rather than being added into the entire layer formulation. Such golf balls and methods would restrict protection against UV degradation to the outermost region of the cover where it is needed, thereby reducing golf ball manufacturing costs and better preserving physical properties. The present inventive golf balls and methods of making same address and solve this need.

SUMMARY OF THE INVENTION

Accordingly, in one embodiment, a golf ball of the invention comprises a layer that is formed from at least one of a thermoset material or a thermoplastic material throughout and has a treated region and an untreated region, wherein the treated region extends inward from an outer surface of the layer and comprises a UV resistance composition, and wherein the untreated region does not comprise the UV resistance composition. The UV resistance composition is formed from a mixture of an ultraviolet light absorber (UVA) and a solvent.

The UVA may be selected, for example, from benzotriazole type stabilizers, hindered amine type stabilizers, phenolic type stabilizers, triazines, or combinations thereof. In a preferred but nonlimiting embodiment, the UVA comprises hydroxyphenyl benzotriazole. The mixture may comprise the UVA in an amount such as from about 2 wt. % to about 30 wt. % of the mixture.

The solvent, meanwhile, may comprise for example at least one of acetone, methyl ethyl ketone, methyl isobutyl ketone, ethyl acetate, or butyl acetate.

The UV resistance composition may further comprise, for example, processing agents, colorants, adhesion promotors, fillers, aliphatic isocyanates, or mixtures thereof.

In one embodiment, the layer is a cover layer. Embodiments are envisioned wherein that cover is surrounded by at least one additional layer. For example, the at least one additional layer may comprises a primer coat surrounded by a finishing coat.

In some embodiments, each additional layer is at least partially transparent or at least partially translucent, or both. In other embodiments at least one of the additional layers is opaque.

In some embodiments, the layer may be an outermost layer. For example, in one embodiment, the layer comprises an outermost coating.

The treated region and untreated region each occupy distinct, discrete and extended spatial locations within the layer, as long as the treated region extends to and within that portion of the layer that would be exposed to UV light. That being said, the untreated region may in some embodiments comprise at least 50% by volume of the layer, or greater than 75% by volume of the layer, or even at least 90% by volume of the layer.

However, embodiments are envisioned wherein the untreated region comprises from about 2% to about 10% by volume of the layer, or from about 5% to about 15% by volume of the layer, or from about 10% to about 25% by volume of the layer, or from 20% to less than about 50% by volume of the layer.

In another embodiment, a golf ball of the invention comprises a layer formed from at least one of a thermoset material or a thermoplastic material throughout and having an outermost region that extends inward from an outer surface of the layer; wherein the outermost region is infused with a UV resistance composition and at least a portion of the layer is not infused with the UV resistance composition. That portion of the layer not being infused with the UV resistance composition may comprise at least 50% by volume of the layer, or greater than 75% by volume of the layer, or even at least 90% by volume of the layer. In one embodiment, the portion of the layer that is not infused with the UV resistance composition may comprise at least about 80% by volume of the layer. Once again, however, embodiments are envisioned wherein the portion of the layer not being infused with the UV resistance composition may comprise from about 2% to about 10% by volume of the layer, or from about 5% to about 15% by volume of the layer, or from about 10% to about 25% by volume of the layer, or from 20% to less than about 50% by volume of the layer.

It is of course conceivable that some of the UV resistance composition could bleed through or otherwise incidentally migrate across an entire thickness or depth of at least a portion of a layer or golf ball component that is treated with the UV resistance composition. In some such cases, a concentration gradient may result within the treated layer or component wherein the concentration of the UV resistance composition decreases inward from treated outer surface. Such a gradient is advantageous since protection is only needed at the surface of the layer which is exposed to harmful UV rays. Cost effectively, in a golf ball of the invention, less UV resistance composition may be used than in conventional golf balls wherein the UV stabilizing composition must be provided and dispersed directly into and throughout the entire layer/component formulation.

Accordingly, in one embodiment of the invention a golf ball of the invention may comprise a layer that is formed from at least one of a thermoset material or a thermoplastic material throughout and has an outer surface that is infused with a UV resistance composition that is formed into the outer surface of the layer sufficient to impart UV resistance at the surface. In this embodiment it is possible that the treated region may comprise at least 50% by volume of the layer due to the aforementioned incidental migration or bleeding.

In yet another embodiment, a golf ball of the invention comprises an outermost layer formed from at least one of a thermoset material or a thermoplastic material throughout and having an outermost region that extends inward from an outer surface of the layer; wherein the outermost region is infused with a UV resistance composition and at least a portion of the layer is not infused with the UV resistance composition.

In one embodiment, a golf ball of the invention may be made by: providing a finished golf ball or a golf ball subassembly having a layer that is formed from at least one of a thermoset material or a thermoplastic material throughout; exposing an outer surface of the layer to a UV resistance composition formed from a mixture of an ultraviolet light absorber (UVA) and a solvent and forming a treated region in the outer surface that extends inward from the outer surface and is infused with the UV resistance composition such that at least a portion of the layer is not infused with the UV resistance composition.

The step of exposing the outer surface to the UV resistance composition may comprise submerging the outer surface in a bath of the UV resistance composition at a temperature of from about 65° F. to about 200° F. for up to about 10 minutes. The method may further include the steps of removing the finished golf ball or golf ball subassembly from the bath, rinsing the outer surface, and drying the outer surface. The drying step may in one embodiment be performed at room temperature for up to 12 hours.

In another embodiment, a golf ball of the invention may be made by providing a layer formed from at least one of a thermoset material or a thermoplastic material throughout; exposing an outer surface of the layer to a UV resistance composition and forming a treated region in the outer surface that extends inward from the outer surface and comprises the UV resistance composition, such that an untreated region of the layer is not exposed to and does not comprise the UV resistance composition.

In yet another embodiment, a golf ball of the invention may be made by providing an outermost layer formed from at least one of a thermoset material or a thermoplastic material throughout; and forming an outermost region in an outer surface of the layer that extends inward from the outer surface and is infused with and comprises a UV resistance composition, such that at least a portion of the outermost layer is not infused with and does not comprise the UV resistance composition.

In still another embodiment, a golf ball of the invention may be made by providing a first layer formed from at least one of a thermoset material or a thermoplastic material throughout; forming an outermost region in an outer surface of the first layer that extends inward from the outer surface and is infused with and comprises a UV resistance composition, such that at least a portion of the outermost layer is not infused with and does not comprise the UV resistance composition; and forming a second layer that is at least partially transparent or translucent about the first layer.

DETAILED DESCRIPTION

The UV resistant and light-stable golf ball of the invention may be manufactured simply and cost effectively by restricting incorporation of the UV resistance composition to those portions of the golf ball that may be exposed to damaging UV light. Protection from UV light damage/yellowing is especially necessary, for example, where the cover, primer and/or finishing coat is formed from a polyurethane-based material. An outermost golf ball surface, normally being directly exposed to UV light on the course, is particularly vulnerable to UV degradation. However, inner layers can also become exposed, for example, through nicks or abrasions that are made by a club such as an iron striking the golf ball during play on the course, or where the outer layer is clear or transparent, for example.

In a golf ball of the invention, the UV resistance composition forms into an outer surface of a layer. Interactions between the UV resistance composition and the outer surface result in forming a shield within the golf ball against the harmful effects of exposure to UV light such as yellowing. In one embodiment, the outer surface is infused with the UV resistance composition by soaking the outer surface in the UV resistance composition.

Illustrative of such golf balls of the invention are golf balls Ex. 1, Ex. 2, Ex. 3, Ex. 4, Ex. 5 and Ex. 6 which are set forth in TABLE I below and compared with one conventional golf ball Comp. Ex. 1 as follows:

TABLE I

| UVA Bath Formulation/ Soaked GB Colorimetric Properties | EXAMPLES | | | | | | |
|---|---|---|---|---|---|---|---|
| | Ex. 1 | Ex. 2 | Ex. 3 | Ex. 4 | Ex. 5 | Ex. 6 | Comp. Ex. 1 |
| UVA Bath | Yes | Yes | Yes | Yes | Yes | Yes | No |
| SONGSORB ®3280[1]:Acetone | 6/94 | 8/92 | 10/90 | — | — | — | — |
| Tinuvin ®571[2]:Acetone | — | — | — | 6/94 | 8/92 | 10/90 | — |
| 30 min. ΔY | 23.15 | 21.89 | 21.83 | 27.35 | 24.19 | 19.76 | 45.79 |
| 30 min. ΔE | 18.66 | 17.56 | 17.48 | 22.37 | 19.66 | 15.8 | 35.62 |
| 60 min. ΔY | 30.06 | 28.36 | 28.89 | 33.63 | 31.15 | 26.53 | 51.71 |
| 60 min. ΔE | 25.07 | 23.41 | 23.87 | 28.39 | 26.2 | 21.87 | 41.35 |

[1]SONGSORB ®3280 is a powder ultraviolet light absorber (UVA) comprised of 2-(2'-hydroxy-3',5'-di-t-amylphenyl) benzotriazole.
[2]Tinuvin ®571 is a liquid UVA of the hydroxyphenyl benzotriazole class.

Inventive golf balls Ex. 1, Ex. 2, Ex. 3, Ex. 4, Ex. 5, Ex. 6 and comparative golf ball Comp. Ex. 1 of TABLE I are identical when the comparison begins. Most importantly, inventive golf balls Ex. 1, Ex. 2, Ex. 3, Ex. 4, Ex. 5, Ex. 6 and comparative golf ball Comp. Ex. 1 each have a cover that is formed from reacting the same prepolymer and curative blend. Specifically, the prepolymer was prepared by reacting of 4,4 MDI with PTMEG 2000 and had a final NCO of 6.5%. Later, 1.05 eq. of prepolymer was reacted with the curative blend consisting of 1.0 eq. of Ethacure 300 and a white dispersion. After molding, all covered golf balls were cured at room temperature for 24 hrs.

Golf balls Ex. 1, Ex. 2, Ex. 3, Ex. 4, Ex. 5, and Ex. 6 were each submerged in a bath consisting of one of the UVA/Acetone mixtures of TABLE I at room temperature for 1 minute, and then removed from the bath, rinsed off with tap water, and dried at room temperature. Notably, upon completion of the drying period, golf balls Ex. 1, Ex. 2, Ex. 3, Ex. 4, Ex. 5, and Ex. 6 each had a treated region in the cover outer surface infused with the UV resistance composition. In contrast, golf ball Comp. Ex. 1 was not so bathed, but instead, set aside for subsequent colorimetry testing once golf balls Ex. 1, Ex. 2, Ex. 3, Ex. 4, Ex. 5, and Ex. 6 are bathed and dried.

In this regard, colorimetry testing for initial color was performed on treated golf balls Ex. 1, Ex. 2, Ex. 3, Ex. 4, Ex. 5, Ex. 6 and comparative golf ball Comp. Ex. 1. Each golf ball was then subjected to UV bombardment for consecutive 30 minute and 60 minute periods. Color measurements were recorded at both the 30 minute and subsequent 60 minute intervals. As shown in TABLE I, golf balls Ex. 1, Ex. 2, Ex. 3, Ex. 4, Ex. 5, and Ex. 6 demonstrated significantly less color change compared with untreated conventional golf ball Comp. Ex. 1.

Although golf balls Ex. 1, Ex. 2, Ex. 3, Ex. 4, Ex. 5, and Ex. 6 of TABLE I were treated by submerging each golf ball in a bath containing a UVA/solvent mixture, numerous other treating techniques are also envisioned for exposing an outer surface of a golf ball layer to the UV resistance composition such as spraying or brushing for example. The UV resistance composition should be applied to a layer's outer surface for a time sufficient for the UV absorber to infuse or penetrate the surface of the layer being treated, which will vary with the layer material being treated, the method of treating, and the particular UV resistance composition being used for treatment of the layer outer surface.

Some treatments can be conducted/performed at room temperature, and others will be conducted at an elevated temperature. In some embodiments, the golf ball/layer may be pre-heated prior to treatment with the UV resistance composition.

Suitable dipping temperatures may range from room temperature to about 200° F., or to about 150° F., or to about 120° F. Meanwhile, submersion/dipping/exposing times may range from about 1 minute to about 15 minutes, or from about 2 minutes to about 10 minutes, or from about 4 minutes to about 8 minutes.

Following treatment, the golf ball layer may be dried of solvent via evaporation at room temperature or in some embodiments by using a post-bake process such as a continuous belt moving through a hot air oven. The drying time sufficient to evaporate the particular solvent will vary based on specific UV resistance composition formulated but will generally range from about 3 minutes to about 30 minutes, or from about 5 minutes to about 20 minutes, or from about 10 minutes to about 15 minutes.

Suitable drying temperatures may range from room temperature to about 250° F., or from about 100° F. to about 200° F., or from about 125° F. to about 150° F.

Importantly, a solvent or solvent blend is suitable where it allows the UV absorber to penetrate the surface of the outer surface without negatively impacting the physical properties of the urethane after evaporation of the solvent. For example, suitable solvents for preparing the UV absorber dipping solution where the cover layer is polyurethane include acetone, methyl ethyl ketone, methyl isobutyl ketone, ethyl acetate, and butyl acetate, etc. Other types of solvents may be added to help with the solubility of the UV absorbers in the solution and penetration into the layer surface.

Thus, a golf ball of the invention with improved UV resistance may be achieved via dipping, soaking or otherwise exposing the molded or painted golf ball or even a sub-assembly to a solution comprising a solvent(s) and UV protective material (s) which creates a shielding layer at or just below the surface region of the layer. The color appearance of golf balls of the invention will be substantially UV light resistant whether the golf ball is white or is a colored golf ball incorporating dyes, pigments, special effect pigments and any other UV light sensitive materials and fillers.

Accordingly, golf balls and methods of this invention are not limited to any particular cover and/or sub-assembly material, and may include all those compositions normally used as a golf ball layer such as ionomers, polyurethanes, polyureas, TPE, HNP, crosslinked rubber, etc., or blends/mixtures thereof. Suitable layer compositions are disclosed, for example, in U.S. Pat. Nos. 6,953,820 and 6,939,907, and U.S. Pat. Nos. 5,919,100, 6,653,382, 6,872,774, 7,074,137, and 7,300,364, the entire disclosures of which are hereby incorporated herein by reference.

Suitable rubber compositions include a base rubber selected from natural and synthetic rubbers, including, but not limited to, polybutadiene, polyisoprene, ethylene propylene rubber ("EPR"), ethylene propylene diene rubber ("EPDM"), styrene butadiene rubber, styrenic block copolymer rubber, butyl rubber, halobutyl rubber, copolymers of isobutylene and para-alkylstyrene, halogenated copolymers of isobutylene and para-alkylstyrene, acrylonitrile butadiene rubber, polychloroprene, alkyl acrylate rubber, chlorinated isoprene rubber, acrylonitrile chlorinated isoprene rubber, polystyrene elastomers, polyethylene elastomers, polyurethane elastomers, polyurea elastomers, metallocene-catalyzed elastomers and plastomers, polyalkenamer, phenol formaldehyde, melamine formaldehyde, polyepoxide, polysiloxane, alkyd, polyisocyanurate, polycyanurate, polyacrylate, and combinations of two or more thereof. Diene rubbers are preferred, particularly polybutadiene, styrene butadiene, acrylonitrile butadiene, and mixtures of polybutadiene with other elastomers wherein the amount of polybutadiene present greater than 40 wt % based on the total polymeric weight of the mixture.

Non-limiting examples of suitable commercially available base rubbers are Buna CB high-cis neodymium-catalyzed polybutadiene rubbers, such as Buna CB 23, Buna CB24, and Buna CB high-cis cobalt-catalyzed polybutadiene rubbers, such as Buna CB 1203, 1220 and 1221, commercially available from Lanxess Corporation; SE BR-1220, commercially available from The Dow Chemical Company; Europrene® NEOCIS® BR 40 and BR 60, commercially available from Polimeri Europa®; UBEPOL-BR® rubbers, commercially available from UBE Industries, Inc.; BR 01, commercially available from Japan Synthetic Rubber Co., Ltd.; Neodene high-cis neodymium-catalyzed polybutadiene rubbers, such as Neodene BR 40, commercially available from Karbochem; TP-301 transpolyisoprene, commercially available from Kuraray Co., Ltd.; Vestenamer® polyoctenamer, commercially available from Evonik Industries; Butyl 065 and Butyl 288 butyl rubbers, commercially available from ExxonMobil Chemical Company; Butyl 301 and Butyl 101-3, commercially available from Lanxess Corporation; Bromobutyl 2224 and Chlorobutyl 1066 halobutyl rubbers, commercially available from ExxonMobil Chemical Company; Bromobutyl X2 and Chlorobutyl 1240 halobutyl rubbers, commercially available from Lanxess Corporation; BromoButyl 2255 butyl rubber, commercially available from Japan Synthetic Rubber Co., Ltd.; Vistalon® 404 and Vistalon® 706 ethylene propylene rubbers, commercially available from ExxonMobil Chemical Company; Dutral CO 058 ethylene propylene rubber, commercially available from Polimeri Europa; Nordel® IP NDR 5565 and Nordel® IP 3670 ethylene-propylene-diene rubbers, commercially available from The Dow Chemical Company; EPT1045 and EPT1045 ethylene-propylene-diene rubbers, commercially available from Mitsui Corporation; Buna SE 1721 TE styrene-butadiene rubbers, commercially available from Lanxess Corporation; Afpol 1500 and Afpol 552 styrene-butadiene rubbers, commercially available from Karbochem; Plioflex PLF 1502, commercially available from Goodyear Chemical; Nipol® DN407 and Nipol® 1041L acrylonitrile butadiene rubbers, commercially available from Zeon Chemicals, L.P.; Neoprene GRT and Neoprene AD30 polychloroprene rubbers; Vamac® ethylene acrylic elastomers, commercially available from E. I. du Pont de Nemours and Company; Hytemp® AR12 and AR214 alkyl acrylate rubbers, commercially available from Zeon Chemicals, L.P.; Hypalon® chlorosulfonated polyethylene rubbers, commercially available from E. I. du Pont de Nemours and Company; and Goodyear Budene® 1207 polybutadiene, commercially available from Goodyear Chemical. In a particular embodiment, the core is formed from a rubber composition comprising as the base rubber a blend of Neodene BR 40 polybutadiene, Budene® 1207 polybutadiene, and Buna SB 1502 styrene butadiene rubber. In another particular embodiment, the core is formed from a rubber composition comprising as the base rubber a blend of Neodene BR 40 polybutadiene, Buna CB 1221, and core regrind.

The rubber is crosslinked using, for example, a peroxide or sulfur cure system, C—C initiators, high energy radiation sources capable of generating free radicals, or a combination thereof. The rubber composition optionally includes one or more of the following: scorch retarder, antioxidant, soft and fast agent, filler, processing aid, processing oil, coloring agent, fluorescent agent, chemical blowing and foaming agent, defoaming agent, stabilizer, softening agent, impact modifier, free radical scavenger, and antiozonant (e.g., p-phenylenediames). Suitable types and amounts of rubber, initiator agent, coagent, filler, and additives are more fully described in, for example, U.S. Pat. Nos. 6,566,483, 6,695, 718, 6,939,907, 7,041,721 and 7,138,460, the entire disclosures of which are hereby incorporated herein by reference. Particularly suitable diene rubber compositions are further disclosed, for example, in U.S. Pat. No. 7,654,918, the entire disclosure of which is hereby incorporated herein by reference.

Suitable ionomer compositions include partially neutralized ionomers and highly neutralized ionomers, including ionomers formed from blends of two or more partially neutralized ionomers, blends of two or more highly neutralized ionomers, and blends of one or more partially neutralized ionomers with one or more highly neutralized ionomers. Preferred ionomers are salts of O/X- and O/X/Y-type acid copolymers, wherein O is an α-olefin, X is a $C_3$-$C_8$ α,β-ethylenically unsaturated carboxylic acid, and Y is a softening monomer. O is preferably selected from ethylene and propylene. X is preferably selected from methacrylic acid, acrylic acid, ethacrylic acid, crotonic acid, and itaconic acid. Methacrylic acid and acrylic acid are particularly preferred. As used herein, "(meth) acrylic acid" means methacrylic acid and/or acrylic acid. Likewise, "(meth) acrylate" means methacrylate and/or acrylate. Y is preferably selected from (meth) acrylate and alkyl (meth) acrylates wherein the alkyl groups have from 1 to 8 carbon atoms, including, but not limited to, n-butyl (meth) acrylate, isobutyl (meth) acrylate, methyl (meth) acrylate, and ethyl (meth) acrylate. Particularly preferred O/X/Y-type copolymers are ethylene/(meth) acrylic acid/n-butyl (meth) acrylate, ethylene/(meth) acrylic acid/isobutyl (meth) acrylate, ethylene/(meth) acrylic acid/methyl (meth) acrylate, and ethylene/(meth) acrylic acid/ethyl (meth) acrylate. The acid is typically present in the acid copolymer in an amount of 6 wt % or greater, or 9 wt % or greater, or 10 wt % or greater, or 11 wt % or greater, or 15 wt % or greater, or 16 wt % or greater, or 19 wt % or greater, or 20 wt % or greater, or in an amount within a range having a lower limit of 1 or 4 or 6 or 8 or 10 or 11 or 12 or 15 wt % and an upper limit of 15 or 16 or 17 or 19 or 20 or 20.5 or 21 or 25 or 30 or 35 or 40 wt %, based on the total weight of the acid copolymer. The acid copolymer is at least partially neutralized with a cation source, optionally in the presence of a high molecular weight organic acid, such as those disclosed in U.S. Pat. No. 6,756,436, the entire disclosure of which is hereby incorporated herein by reference. In a particular embodiment, less than 40% of the acid groups present in the composition are neutralized. In another particular embodiment, from 40% to 60% of the acid groups present in the composition are neutralized. In another particular embodiment, from 60% to 70% of the acid groups present in the composition are neutralized. In another particular embodiment, from 60% to 80% of the acid groups present in the composition are neutralized. In another particular embodiment, from 70% to 80% of the acid groups present in the composition are neutralized. In another embodiment, from 80% to 100% of the acid groups present in the composition are neutralized. Suitable cation sources include, but are not limited to, metal ion sources, such as compounds of alkali metals, alkaline earth metals, transition metals, and rare earth elements; ammonium salts and monoamine salts; and combinations thereof. Preferred cation sources are compounds of magnesium, sodium, potassium, cesium, calcium, barium, manganese, copper, zinc, tin, lithium, and rare earth metals. In a particular embodiment, the ionomer composition includes a bimodal ionomer, for example, DuPont® AD1043 ionomers, and the ionomers disclosed in U.S. Pat. No. 7,037,967 and U.S. Pat. Nos. 6,562,906, 6,762,246 and 7,273,903, the entire disclosures of which are hereby incorporated herein by reference. Suitable ionomers are further disclosed, for example, in U.S. Pat. Nos. 5,587,430, 5,691,418, 5,866,658, 6,100,321, 6,653,382, 6,756,436, 6,777,472, 6,815,480, 6,894,098, 6,919,393, 6,953,820, 6,994,638, 7,230,045, 7,375,151, 7,429,624, and 7,652,086, the entire disclosures of which are hereby incorporated herein by reference.

Suitable ionomer compositions also include blends of one or more partially- or fully-neutralized polymers with additional thermoplastic and thermoset materials, including, but not limited to, non-ionomeric acid copolymers, engineering thermoplastics, fatty acid/salt-based highly neutralized polymers, polybutadienes, polyurethanes, polyureas, polyesters, polyamides, polycarbonate/polyester blends, thermoplastic elastomers, maleic anhydride-grafted metallocene-catalyzed polymers (e.g., maleic anhydride-grafted metallocene-catalyzed polyethylene), and other conventional polymeric materials.

Suitable ionomeric compositions are further disclosed, for example, in U.S. Pat. Nos. 6,653,382, 6,756,436, 6,777,472, 6,894,098, 6,919,393, and 6,953,820, the entire disclosures of which are hereby incorporated herein by reference.

Also suitable are polyester ionomers, including, but not limited to, those disclosed, for example, in U.S. Pat. Nos. 6,476,157 and 7,074,465, the entire disclosures of which are hereby incorporated herein by reference.

Also suitable are thermoplastic elastomers comprising a silicone ionomer, as disclosed, for example, in U.S. Pat. No. 8,329,156, the entire disclosure of which is hereby incorporated herein by reference.

Also suitable are the following non-ionomeric polymers, including homopolymers and copolymers thereof, as well as their derivatives that are compatibilized with at least one grafted or copolymerized functional group, such as maleic anhydride, amine, epoxy, isocyanate, hydroxyl, sulfonate, phosphonate, and the like:

(a) polyesters, particularly those modified with a compatibilizing group such as sulfonate or phosphonate, including modified poly(ethylene terephthalate), modified poly(butylene terephthalate), modified poly(propylene terephthalate), modified poly(trimethylene terephthalate), modified poly(ethylene naphthenate), and those disclosed in U.S. Pat. Nos. 6,353,050, 6,274,298, and 6,001,930, the entire disclosures of which are hereby incorporated herein by reference, and blends of two or more thereof;

(b) polyamides, polyamide-ethers, and polyamide-esters, and those disclosed in U.S. Pat. Nos. 6,187,864, 6,001,930, and 5,981,654, the entire disclosures of which are hereby incorporated herein by reference, and blends of two or more thereof;

(c) polyurethanes, polyureas, polyurethane-polyurea hybrids, and blends of two or more thereof;

(d) fluoropolymers, such as those disclosed in U.S. Pat. Nos. 5,691,066, 6,747,110 and 7,009,002, the entire disclosures of which are hereby incorporated herein by reference, and blends of two or more thereof;

(e) non-ionomeric acid polymers, such as E/X- and E/X/Y-type copolymers, wherein E is an olefin (e.g., ethylene), X is a carboxylic acid such as acrylic, methacrylic, crotonic, maleic, fumaric, or itaconic acid, and Y is an optional softening comonomer such as vinyl esters of aliphatic carboxylic acids wherein the acid has from 2 to 10 carbons, alkyl ethers wherein the alkyl group has from 1 to 10 carbons, and alkyl alkylacrylates such as alkyl methacrylates wherein the alkyl group has from 1 to 10 carbons; and blends of two or more thereof;

(f) metallocene-catalyzed polymers, such as those disclosed in U.S. Pat. Nos. 6,274,669, 5,919,862, 5,981,654, and 5,703,166, the entire disclosures of which are hereby incorporated herein by reference, and blends of two or more thereof;

(g) polystyrenes, such as poly(styrene-co-maleic anhydride), acrylonitrile-butadiene-styrene, poly(styrene sulfonate), polyethylene styrene, and blends of two or more thereof;

(h) polypropylenes and polyethylenes, particularly grafted polypropylene and grafted polyethylenes that are modified with a functional group, such as maleic anhydride of sulfonate, and blends of two or more thereof;

(i) polyvinyl chlorides and grafted polyvinyl chlorides, and blends of two or more thereof;
(j) polyvinyl acetates, preferably having less than about 9% of vinyl acetate by weight, and blends of two or more thereof;
(k) polycarbonates, blends of polycarbonate/acrylonitrile-butadiene-styrene, blends of polycarbonate/polyurethane, blends of polycarbonate/polyester, and blends of two or more thereof;
(l) polyvinyl alcohols, and blends of two or more thereof;
(m) polyethers, such as polyarylene ethers, polyphenylene oxides, block copolymers of alkenyl aromatics with vinyl aromatics and poly(amic ester)s, and blends of two or more thereof;
(n) polyimides, polyetherketones, polyamideimides, and blends of two or more thereof;
(o) polycarbonate/polyester copolymers and blends; and
(p) combinations of any two or more of the above thermoplastic polymers.

Examples of commercially available thermoplastics suitable for forming thermoplastic layers include, but are not limited to, Pebax® thermoplastic polyether block amides, commercially available from Arkema Inc.; Surlyn® ionomer resins, Hytrel® thermoplastic polyester elastomers, and ionomeric materials sold under the trade names DuPont® HPF 1000, HPF 2000, HPF AD 1035, HPF AD 1040, all of which are commercially available from E. I. du Pont de Nemours and Company; Iotek® ionomers, commercially available from ExxonMobil Chemical Company; Amplify® IO ionomers of ethylene acrylic acid copolymers, commercially available from The Dow Chemical Company; Clarix® ionomer resins, commercially available from A. Schulman Inc.; Elastollan® polyurethane-based thermoplastic elastomers, commercially available from BASF; and Xylex® polycarbonate/polyester blends, commercially available from SABIC Innovative Plastics.

Suitable plasticized polymer compositions include a plasticizer in an amount sufficient to substantially change the stiffness and/or hardness of the composition, and typically comprise from 20 to 99.5 wt % of the polymer and from 0.5 to 80 wt % of the plasticizer, based on the combined weight of the polymer and the plasticizer. In a particular embodiment, the plasticizer is present in an amount of 0.5% or 1% or 3% or 5% or 7% or 8% or 9% or 10% or 12% or 15% or 18% or 20% or 22% or 25% or 30% or 35% or 40% or 42% or 50% or 55% or 60% or 66% or 71% or 75% or 80%, by weight based on the combined weight of the polymer and the plasticizer, or the plasticizer is present in an amount within a range having a lower limit and an upper limit selected from these values. Suitable polymers include acid copolymers, partially neutralized acid copolymers, highly neutralized acid polymers ("HNPs"), polyesters, polyamides, thermosetting and thermoplastic polyurethanes.

Suitable plasticized acid copolymer compositions, plasticized partially neutralized acid copolymer compositions, and plasticized HNP compositions, and particularly suitable golf ball constructions utilizing such compositions, are further disclosed, for example, in U.S. Patent Application Publ. No. 2015/0031475, U.S. Patent Application Publ. No. 2015/0005108, U.S. patent application Ser. No. 14/576,800, and U.S. patent application Ser. No. 14/588,317, the entire disclosures of which are hereby incorporated herein by reference.

Suitable plasticized polyester compositions, and particularly suitable golf ball constructions utilizing such compositions, are further disclosed, for example, in U.S. patent application Ser. No. 14/532,141, the entire disclosure of which is hereby incorporated herein by reference.

Suitable plasticized polyamide compositions, and particularly suitable golf ball constructions utilizing such compositions, are further disclosed, for example, in U.S. Patent Application Publ. No. 2014/0302947, U.S. Patent Application Publ. No. 2014/0323243, U.S. Patent Application Publ. No. 20150057105, and U.S. patent application Ser. No. 14/576,324, the entire disclosures of which are hereby incorporated herein by reference.

Suitable plasticized polyurethane compositions, and particularly suitable golf ball constructions utilizing such compositions, are further disclosed, for example, in U.S. patent application Ser. No. 14/672,538, U.S. patent application Ser. No. 14/672,523, U.S. patent application Ser. No. 14/672,485, and U.S. patent application Ser. No. 14/691,720, the entire disclosures of which are hereby incorporated herein by reference. Further suitable plasticized compositions include for example those disclosed in U.S. patent application Ser. Nos. 14/571,610, 14/576,324, and 14/707,028.

And it is contemplated that a golf ball of the invention may have any known construction and have any number of layers with any known properties. In one non-limiting example, a golf ball of the invention may comprise a single core having a diameter of from about 1.20 in. to about 1.65 in. Alternatively, the core may have a dual core arrangement having a total diameter of from about 1.40 in. to about 1.65 in, for example, wherein the inner core may has a diameter of from about 0.75 inches to about 1.30 in. and the outer core has a thickness of from about 0.05 in. to about 0.45 in. Cover thicknesses generally range from about 0.015 in. to about 0.090 inches, although a golf ball of the invention may comprise any known thickness. Meanwhile, casing layers and inner cover layers each typically have thicknesses ranging from about 0.01 in. to about 0.06 in. A golf ball of the invention may also have one or more film layers, paint layers or coating layers having a combined thickness of from about 0.1 µm to about 100 µm, or from about 2 µm to about 50 µm, or from about 2 µm to about 30 µm. Meanwhile, each coating layer may have a thickness of from about 0.1 µm to about 50 µm, or from about 0.1 µm to about 25 µm, or from about 0.1 µm to about 14 µm, or from about 2 µm to about 9 µm, for example.

A golf ball of the invention may further incorporate indicia, which as used herein, is considered to mean any symbol, letter, group of letters, design, or the like, that can be added to the dimpled surface of a golf ball.

It will be appreciated that any known dimple pattern may be used with any number of dimples having any shape or size. For example, the number of dimples may be 252 to 456, or 330 to 392 and may comprise any width, depth, and edge angle. The parting line configuration of said pattern may be either a straight line or a staggered wave parting line (SWPL), for example.

In any of these embodiments the single-layer core may be replaced with a two or more layer core wherein at least one core layer has a hardness gradient. And the cover hardness may be targeted depending on desired playing characteristics. As a general rule, all other things being equal, a golf ball having a relatively soft cover will spin more than a similarly constructed ball having a harder cover.

In the present invention, compression and CoR may also be tailored to suit desired playing characteristics. In this regard, "compression" is measured according to a known procedure, using an Atti compression test device, wherein a piston is used to compress a ball against a spring. The travel of the piston is fixed and the deflection of the spring is measured. The measurement of the deflection of the spring does not begin with its contact with the ball; rather, there is an offset of approximately the first 1.25 mm (0.05 inches) of the spring's deflection. Cores having a very low stiffness will not cause the spring to deflect by more than 1.25 mm and therefore have a zero compression measurement. The Atti compression tester is designed to measure objects having a diameter of 1.680 inches; thus, smaller objects, such as golf ball cores, must be shimmed to a total height of 1.680 inches to obtain an accurate reading. Conversion from Atti compression to Riehle (cores), Riehle (balls), 100 kg deflection, 130-10 kg deflection or effective modulus can be carried out according to the formulas given in J. Dalton, *Compression by Any Other Name, Science and Golf IV, Proceedings of the World Scientific Congress of Golf* (Eric Thain ed., Routledge, 2002) ("J. Dalton").

In a golf ball if the invention, Coefficient of Restitution or COR is determined according to a known procedure, wherein a golf ball or golf ball subassembly (for example, a golf ball core) is fired from an air cannon at two given velocities and a velocity of 125 ft/s is used for the calculations. Ballistic light screens are located between the air cannon and steel plate at a fixed distance to measure ball velocity. As the ball travels toward the steel plate, it activates each light screen and the ball's time period at each light screen is measured. This provides an incoming transit time period which is inversely proportional to the ball's incoming velocity. The ball makes impact with the steel plate and rebounds so it passes again through the light screens. As the rebounding ball activates each light screen, the ball's time period at each screen is measured. This provides an outgoing transit time period which is inversely proportional to the ball's outgoing velocity. COR is then calculated as the ratio of the outgoing transit time period to the incoming transit time period, $COR=V_{out}/V_{in}=T_{in}/T_{out}$. The COR value can be targeted, for example, by varying the core peroxide and antioxidant types and amounts as well as the cure temperature and duration.

The surface hardness of a golf ball layer is obtained from the average of a number of measurements taken from opposing hemispheres, taking care to avoid making measurements on the parting line of the core or on surface defects such as holes or protrusions. Hardness measurements are made pursuant to ASTM D-2240 "Indentation Hardness of Rubber and Plastic by Means of a Durometer." Because of the curved surface of the golf ball layer, care must be taken to ensure that the golf ball or golf ball subassembly is centered under the durometer indentor before a surface hardness reading is obtained. A calibrated digital durometer, capable of reading to 0.1 hardness units, is used for all hardness measurements. The digital durometer must be attached to and its foot made parallel to the base of an automatic stand. The weight on the durometer and attack rate conforms to ASTM D-2240. It should be understood that there is a fundamental difference between "material hardness" and "hardness as measured directly on a golf ball." For purposes of the present invention, material hardness is measured according to ASTM D2240 and generally involves measuring the hardness of a flat "slab" or "button" formed of the material. Surface hardness as measured directly on a golf ball (or other spherical surface) typically results in a different hardness value. The difference in "surface hardness" and "material hardness" values is due to several factors including, but not limited to, ball construction (that is, core type, number of cores and/or cover layers, and the like); ball (or sphere) diameter; and the material composition of adjacent layers. It also should be understood that the two measurement techniques are not linearly related and, therefore, one hardness value cannot easily be correlated to the other.

It is understood that the golf balls of the invention incorporating at least one treated surface as described and illustrated herein represent only some of the many embodiments of the invention. It is appreciated by those skilled in the art that various changes and additions can be made to such golf balls without departing from the spirit and scope of this invention. It is intended that all such embodiments be covered by the appended claims.

Other than in the operating examples, or unless otherwise expressly specified, all of the numerical ranges, amounts, values and percentages such as those for amounts of materials and others in the specification may be read as if prefaced by the word "about" even though the term "about" may not expressly appear with the value, amount or range. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used.

Although the golf ball of the invention has been described herein with reference to particular means and materials, it is to be understood that the invention is not limited to the particulars disclosed and extends to all equivalents within the scope of the claims.

What is claimed is:

1. A method of making a golf ball comprising:
   providing a finished golf ball or a golf ball subassembly, having a layer that is formed from a thermoset polyurethane material throughout;
   exposing an outer surface of the layer at room temperature to a UV resistance composition that is formed from a mixture of an ultraviolet light absorber (UVA) and a solvent; and
   forming a treated region in the layer that is infused with the UV resistance composition and extends inward from the outer surface and an untreated region of the layer that is not infused with the UV resistance composition.

2. The method of making a golf ball of claim 1, wherein the step of exposing the outer surface to the UV resistance composition comprises submerging the outer surface in a bath of the UV resistance composition for up to about 10 minutes.

3. The method of making a golf ball of claim 2, further comprising the steps of:
   removing the finished golf ball or golf ball subassembly from the bath;
   rinsing the outer surface; and
   drying the outer surface.

4. The method of making a golf ball of claim 1, wherein the UVA is selected from benzotriazole type stabilizers, hindered amine type stabilizers, phenolic type stabilizers, triazines, or combinations thereof.

5. The method of making a golf ball of claim 4, wherein the UVA comprises hydroxyphenyl benzotriazole.

6. The method of making a golf ball of claim 4, wherein the solvent comprises at least one of acetone, methyl ethyl ketone, methyl isobutyl ketone, ethyl acetate, or butyl acetate.

7. The method of making a golf ball of claim 6, wherein the mixture comprises the UVA in an amount of from about 2 wt. % to about 30 wt. % of the mixture.

8. The method of making a golf ball of claim 7, wherein the layer is a cover layer.

9. The method of making a golf ball of claim 8, wherein the cover is surrounded by at least one additional layer.

10. The method of making a golf ball of claim 9, wherein the at least one additional layer comprises a primer coat surrounded by a finishing coat.

11. The method of making a golf ball of claim 9, wherein each additional layer is at least partially transparent or at least partially translucent, or both.

12. The method of making a golf ball of claim 7, wherein the layer comprises an outermost layer.

13. The method of making a golf ball of claim 12, wherein the outermost layer comprises a coating.

14. The method of making a golf ball of claim 7, wherein the untreated region comprises at least 50% by volume of the layer.

15. The method of making a golf ball of claim 7, wherein the untreated region comprises at least 90% by volume of the layer.

16. The method of making a golf ball of claim 7, wherein the treated region comprises at least 50% by volume of the layer.

* * * * *